(12) United States Patent
Stone

(10) Patent No.: US 11,638,537 B2
(45) Date of Patent: May 2, 2023

(54) WEARABLE PHYSIOLOGICAL MONITORING SYSTEM

(71) Applicant: Medical Design Solutions, Inc., Milpitas, CA (US)

(72) Inventor: Robert T Stone, Sunnyvale, CA (US)

(73) Assignee: Medical Design Solutions, Inc., Milpitas, CA (US)

( * ) Notice: Subject to any disclaimer, the term of this patent is extended or adjusted under 35 U.S.C. 154(b) by 2 days.

(21) Appl. No.: 17/518,053

(22) Filed: Nov. 3, 2021

(65) Prior Publication Data

US 2022/0061697 A1 Mar. 3, 2022

Related U.S. Application Data

(63) Continuation of application No. 16/419,358, filed on May 22, 2019, now Pat. No. 11,191,452, which is a (Continued)

(51) Int. Cl.
*A61B 5/08* (2006.01)
*A61B 5/091* (2006.01)
(Continued)

(52) U.S. Cl.
CPC ............... *A61B 5/091* (2013.01); *A61B 5/01* (2013.01); *A61B 5/08* (2013.01); *A61B 5/1135* (2013.01); *A61B 5/6804* (2013.01); *A61B 5/6805* (2013.01); *A61B 5/6831* (2013.01); *A61B 5/7257* (2013.01); *A61B 5/742* (2013.01); *A61B 5/02055* (2013.01); *A61B 2562/0223* (2013.01)

(58) Field of Classification Search
CPC .... A61B 2562/0219; A61B 2562/0223; A61B 5/01; A61B 5/0205; A61B 5/02055; A61B 5/05; A61B 5/08; A61B 5/091; A61B 5/1116; A61B 5/1135; A61B 5/14542; A61B 5/4806; A61B 5/6804; A61B 5/6805; A61B 5/6831; A61B 5/7257; A61B 5/742
See application file for complete search history.

(56) References Cited

U.S. PATENT DOCUMENTS

| | | | |
|---|---|---|---|
| 2010/0145236 A1* | 6/2010 | Greenberg | G01S 19/42 600/595 |
| 2011/0050216 A1* | 3/2011 | Stone | G01R 33/02 324/244 |

(Continued)

*Primary Examiner* — Eric J Messersmith
(74) *Attorney, Agent, or Firm* — Francis Law Group

(57) ABSTRACT

A wearable respiration monitoring system having a transmitter coil that is adapted to generate and transmit multi-frequency AC magnetic fields, a receiver coil adapted to detect variable strengths in one of the AC magnetic fields and generate AC magnetic field strength signals representing anatomical displacements of a monitored subject, and at least one accelerometer that is configured to detect and monitor anatomical positions and movement of the subject, and generate and transmit accelerometer signals representing same. The wearable monitoring system further includes an electronics module that is adapted to receive the AC magnetic field strength signals and accelerometer signals, and determine at least one respiratory disorder as a function of the AC magnetic field strength signals and at least one anatomical position of the subject as a function of the accelerometer signals.

18 Claims, 5 Drawing Sheets

Related U.S. Application Data continuation-in-part of application No. 16/363,404, filed on Mar. 25, 2019, now Pat. No. 10,993,638, and a continuation-in-part of application No. 16/117,921, filed on Aug. 30, 2018, now Pat. No. 10,314,517, and a continuation of application No. 15/133,497, filed on Apr. 20, 2016, now Pat. No. 10,064,570, and a continuation-in-part of application No. 13/854,280, filed on Apr. 1, 2013, now abandoned.

(51) Int. Cl.
*A61B 5/00* (2006.01)
*A61B 5/01* (2006.01)
*A61B 5/113* (2006.01)
*A61B 5/0205* (2006.01)

(56) References Cited

U.S. PATENT DOCUMENTS

| | | | |
|---|---|---|---|
| 2011/0054271 A1* | 3/2011 | Derchak | A61B 5/389 600/595 |
| 2011/0054272 A1* | 3/2011 | Derchak | A61B 5/369 600/301 |
| 2011/0130643 A1* | 6/2011 | Derchak | A63B 24/0006 600/534 |
| 2013/0314081 A1* | 11/2013 | Igney | G01N 27/023 324/239 |

\* cited by examiner

WEARABLE PHYSIOLOGICAL MONITORING SYSTEM

CROSS-REFERENCES TO RELATED APPLICATIONS

This application is a continuation of U.S. application Ser. No. 16/419,358, filed on May 22, 2019, which is a continuation-in-part of U.S. application Ser. No. 16/363,404, filed on Mar. 25, 2019, now U.S. Pat. No. 10,993,638, which is a continuation-in-part of U.S. application Ser. No. 16/117,921, filed on Aug. 30, 2018, now U.S. Pat. No. 10,314,517, which is a continuation of U.S. application Ser. No. 15/133,497, filed on Apr. 20, 2016, now U.S. Pat. No. 10,064,570, which is a continuation-in-part of U.S. application Ser. No. 13/854,280, filed on Apr. 1, 2013, now abandoned.

FIELD OF THE INVENTION

The present invention relates to systems and methods for monitoring physiological characteristics of a subject. More particularly, the present invention relates to apparatus, systems and methods for determining a plurality of physiological characteristics; particularly, respiratory characteristics of a subject and respiratory disorders exhibited thereby, and anatomical positions and motions of the subject.

BACKGROUND OF THE INVENTION

It is well known in the art that approximately 10% of adults are affected by a respiratory disorder. Most respiratory disorders are deemed a serious risk factor because they can, and often will, have a long-term effect on the cardiovascular system. Indeed, sympathetic modulation has been found to be closely related to adverse heart rate variability, e.g., cardiac arrhythmia.

The most common respiratory disorders that affect adults are sleep apneas and hypopnea.

As is well known in the art, sleep apnea is generally classified into three types based on respiratory functions. The first type of apnea is obstructive sleep apnea (OSA), which occurs when the subject or patient stops breathing continuously due to an obstructed upper airway.

The second type of apnea is central sleep apnea (CEN), which occurs when the subject or patient stops breathing continuously due to the inability of the subject to correctly modulate respiration, i.e., the brain temporarily fails to transmit appropriate neurological signals to the muscles responsible for controlling breathing. Unlike obstructive sleep apnea, which can be thought of as a mechanical problem, central sleep apnea is more of a communication problem.

The third type of apnea is generally referred to as mixed apnea, which is a combination of obstructive and central sleep apnea. Mixed apnea is generally characterized by a lack of respiratory effort without air exchange due to upper airway obstruction.

Hypopnea is a respiratory disorder that is characterized by overly shallow breathing or an abnormally low respiration rate, i.e., a decreased amount of air movement into the lungs, which can, and often will cause oxygen levels in the blood to drop.

As is also well known in the art, various abnormal seminal respiratory parameters and/or characteristics, such as breathing frequency (e.g., breaths per minute), tidal volume ($V_T$), inspiration volume, expiration volume, respiratory minute ventilation (e.g., inspiration volume per minute or expiration volume per minute) and/or peak expiratory flow rate, and physiological parameters and/or characteristics, such as oxyhemoglobin saturation and oxygen desaturation index, are indicative of a sleep apnea and/or hypopnea.

Various systems and methods have thus been developed to detect one or more respiratory parameters and determine a respiratory disorder, such as sleep apnea, therefrom. Most of the systems and methods are based on anatomical displacements and the relationships thereof to one or more of the above referenced respiratory parameters and characteristics, e.g., breathing frequency, $V_T$ and inspiration volume.

Illustrative are the systems and methods for determining respiratory parameters disclosed in U.S. Pat. Nos. 8,790,273 and 8,790,274 (hereinafter "McCool patents"). The systems disclosed in the referenced McCool patents generally comprise at least two tuned pairs of electromagnetic (EM) coils (also referred to herein as "magnetometers"), where each pair of EM coils comprise a single-channel transmitter EM coil that is adapted to transmit a single, specific high-frequency AC electromagnetic field (i.e., transducer) and an EM coil (i.e., receiver) that is adapted to receive the AC electromagnetic field transmitted by the transmitter EM coil.

The transmitter EM coil(s) of the McCool systems are positioned on the front of a subject and the receiver EM coils are positioned on the back of the subject.

The systems disclosed in the McCool patents are configured to determine at least one respiratory parameter or characteristic; particularly, tidal volume ($V_T$) as a function of a plurality of anatomical distances, e.g., rib cage-anteroposterior distance and abdomen-anteroposterior distance, which are detected by the tuned pairs of EM coils, and a plurality of predetermined volume-motion coefficients.

A major drawback and disadvantage associated with the McCool systems and associated methods is the use of single-channel transmitter EM coils that (i) are limited to one (1) specific AC electromagnetic field frequency and (ii) are susceptible to interference from extraneous electromagnetic fields that negatively impact the voltage output of the EM coils and, hence, the consistency of the AC electromagnetic field frequency.

A further drawback and disadvantage associated with the McCool systems is that the McCool systems and associated methods are dependent on the use of complex algorithms, which can, and often will, fail to quantitatively account for physiological differences between individual subjects. As a result, the McCool systems are incapable of consistently providing accurate determinations of seminal physiological parameters and/or characteristics, such as tidal volume ($V_T$) and minute ventilation (V-dot).

Another drawback and disadvantage associated with the McCool systems is the extensive amount of cumbersome wiring that is required for the McCool systems to operate.

Further systems and methods for determining respiratory parameters and respiratory disorders associated therewith are disclosed in Applicant's issued U.S. Pat. No. 10,064,570, and U.S. application Ser. No. 16/117,921, now U.S. Pat. No. 10,314,517.

In contrast to the McCool systems, the systems disclosed in U.S. Pat. Nos. 10,064,570 and 10,314,517 comprise at least one permanent magnet coupled with at least one magnetometer that is configured to receive the AC electromagnetic field generated by the permanent magnet. The magnetometer is positioned on the front of a subject proximate the xyphoid process and the permanent magnet is positioned on the back of the subject proximate the spine and across from the xyphoid process of the subject.

The magnetometer of the above noted systems is adapted to detect strength variations in the AC magnetic field emitted by the permanent magnet, which reflect displacements, i.e., change in distance, by and between the magnetometer and permanent magnet and, hence, the axial displacements of the chest wall of the subject. The systems are then programmed and configured to determine at least one respiratory parameter of the subject as a function of the axial displacements of the subject's chest wall.

A seminal advantage of the systems disclosed in U.S. Pat. Nos. 10,064,570 and 10,314,517 comprises the use of a permanent rare earth magnet that is capable of generating an AC magnetic field with a substantially higher degree of magnetic field strength per unit mass compared to conventional magnetic field transducers.

Further advantages provided by the permanent rare earth magnet are that the permanent magnet is capable of providing an AC magnetic field with (i) a greater degree of magnetic field stability over time compared to conventional magnetic field transducers and (ii) that is minimally impacted by interference from extraneous electromagnetic fields compared to conventional magnetic field transducers. The systems disclosed in U.S. Pat. Nos. 10,064,570 and 10,314,517 are thus capable of measuring multiple respiratory parameters associated with a user or wearer with a high degree of accuracy, while minimizing inference from external sources, such as electromagnetic radiation.

Further, since permanent rare earth magnets do not require an external power source or control module to generate an AC magnetic field, the systems disclosed in U.S. Pat. Nos. 10,064,570 and 10,314,517 require substantially less wiring and electrical power to operate compared to conventional systems, such as the systems disclosed by McCool.

Although the systems disclosed in U.S. Pat. Nos. 10,064,570 and 10,314,517 can be readily employed to accurately determine multiple respiratory parameters in real time and determine respiratory disorders; particularly, apneas and hypopnea therefrom, it is desirable to provide an improved system based thereon with enhanced respiratory and physiological parameter detection accuracy and, thereby, respiratory disorder determination.

It is also well known in the art that the anatomical position of a subject during sleep can, and in many instances will, induce an adverse action by the subject, e.g., gastrointestinal regurgitation, or exasperate an existing condition of the subject, e.g., sleep apnea.

At present there are few, if any, apparatus and/or systems available that are configured to accurately monitor anatomical positions and movements of a subject during sleep.

There is thus a need to provide improved physiological monitoring systems that accurately detect and measure respiratory parameters and/or characteristics in real time based on anatomical displacements of a monitored subject.

There is also a need to provide apparatus and systems that are capable of accurately detecting and monitoring anatomical positions and movements of a subject during sleep.

It is therefore an object of the present invention to provide a wearable physiological monitoring system that accurately detects and measures respiratory parameters and/or characteristics in real time based on anatomical displacements of a monitored subject.

It is another object of the present invention to provide a wearable physiological monitoring system that accurately detects and measures respiratory and physiological parameters and characteristics in real time based on anatomical displacements of a monitored subject.

It is another object of the present invention to provide a wearable physiological monitoring system that accurately determines anatomical positions of a subject.

It is another object of the present invention to provide improved methods for determining a respiratory disorder based on detected respiratory and/or physiological parameters and/or characteristics.

It is another object of the present invention to provide improved methods for determining sleep apnea and/or hypopnea based on detected abnormal respiratory and/or physiological parameters and/or characteristics.

SUMMARY OF THE INVENTION

The present invention is directed to wearable physiological monitoring systems and improved methods for determining (i) respiratory and/or sleep disorders based on measured anatomical displacements and measured physiological parameters and/or characteristics, and (ii) anatomical positions and movement of a subject.

In a preferred embodiment of the invention, the wearable physiological monitoring systems comprise a wearable garment that is configured to cover at least the chest region and upper back of a subject (or user).

In a preferred embodiment of the invention, the wearable physiological monitoring systems comprise a respiratory parameter monitoring sub-system, an electronics, i.e., control-processing, module, and integral signal transmission means associated therewith.

In some embodiments of the invention, the wearable physiological monitoring systems further comprise a physiological parameter monitoring sub-system.

In some embodiments of the invention, the respiratory parameter monitoring sub-system comprises at least one transmitter coil and multiple receiver coils.

In a preferred embodiment of the invention, the respiratory parameter monitoring sub-system comprises at least one transmitter coil and at least one receiver coil.

In some embodiments of the invention, the physiological parameter monitoring sub-system further comprises an accelerometer that is configured and positioned to establish at least one anatomical position of the subject and monitor physical movement of the subject.

In a preferred embodiment of the invention, the electronics module comprises a multi-channel module that is programmed and configured (i.e., comprises programs, parameters, instructions and at least one algorithm) to control the physiological monitoring systems.

In some embodiments of the invention, the electronics module is preferably programmed and configured to (i) receive AC magnetic field strength signals that are generated and transmitted by the receiver coils, (ii) identify the frequency of each of the associated AC magnetic field strength signals, (iii) determine the identity of the receiver coil based on the frequency of the AC magnetic field strength signals, (iv) determine at least one respiratory parameter, more preferably, a plurality of respiratory parameters associated with the monitored subject as a function of the AC magnetic field strength signals, (v) determine at least one respiratory parameter value as a function of the AC magnetic field strength signals, and (vi) determine at least one respiratory disorder as a function of the determined respiratory parameter and determined value thereof.

In some embodiments of the invention, the electronics module is further programmed and configured to (i) receive at least one respiratory parameter signal representing a pre-measured baseline respiratory parameter value, and (ii)

determine at least one respiratory disorder as a function of the pre-measured baseline respiratory parameter value and the respiratory parameter and value thereof determined as a function of the AC magnetic field strength signals.

In some embodiments, the electronics module is further programmed and configured to receive and process physiological parameter signals representing physiological parameter values of a subject that are generated and transmitted by the physiological parameter monitoring sub-system, i.e., a physiological parameter sensor thereof.

In some embodiments of the invention, the electronics module is preferably programmed and configured to (i) receive AC magnetic field strength signals that are transmitted by the receiver coils and physiological parameter signal(s) transmitted by a physiological parameter sensor, (ii) identify the frequency of each of the AC magnetic field strength signals, (iii) determine the identity of the receiver coil based on the frequency of the AC magnetic field strength signals, (iv) determine at least one respiratory parameter, more preferably, a plurality of respiratory parameters associated with the monitored subject as a function of the AC magnetic field strength signals, (v) determine at least one respiratory parameter value as a function of the AC magnetic field strength signals, and (vi) determine at least one respiratory disorder as a function of the physiological parameter value, and the respiratory parameter and value thereof determined as a function of the AC magnetic field strength signals.

In some embodiments, the electronics module is further programmed and configured to (i) receive accelerometer signals representing the anatomical position and movement data of the monitored subject that are generated and transmitted by an accelerometer, and (ii) determine at least one respiratory disorder as a function of the pre-measured baseline respiratory parameter value, physiological parameter value, accelerometer data, and the respiratory parameter and value thereof determined as a function of the AC magnetic field strength signals.

In some embodiments, the electronics module is further programmed and configured to determine at least one anatomical position of the monitored subject as a function of the accelerometer data.

In some embodiments of the invention, the electronics module is also programmed and configured to generate and transmit at least one anatomical position warning signal as a function of (or in response to) the determined anatomical position and a pre-determined anatomical position of the subject, e.g., erect, semi-erect, left lateral recumbent lying, right lateral recumbent lying, supine or prone position.

In a preferred embodiment, the anatomical position warning signal induces excitation or warning events that are configured to prompt a subject to transition to an alternative position that is less likely to exacerbate and/or trigger a symptom of an existing respiratory or sleep disorder of the subject, e.g., obstructive sleep apnea or gastroesophageal reflux disease.

In some embodiments of the invention, the physiological monitoring systems further comprise a vibration device that is configured to receive the anatomical position warning signal and generate a vibration at a pre-determined frequency in response to the anatomical position warning signal.

In some embodiments of the invention, the physiological monitoring systems further comprise an integral audio device that is configured to receive the anatomical position warning signal and generate an audible signal at a pre-determined amplitude in response to the anatomical position warning signal.

In some embodiments of the invention, the physiological monitoring systems further comprise a remote audio device that is configured to receive the anatomical position warning signal and generate an audible signal at a pre-determined amplitude in response to the anatomical position warning signal.

In some embodiments of the invention, the method for determining a respiratory disorder and anatomical position of the subject generally comprises:

(i) providing a wearable physiological monitoring system of the invention;

(ii) positioning the wearable physiological monitoring system on the subject;

(iii) initiating the wearable physiological monitoring system, wherein AC magnetic fields are generated and transmitted by the transmitter coil, the AC magnetic fields comprising predetermined frequencies;

(iv) detecting and measuring strengths in an AC magnetic field with a receiver coil;

(v) generating AC magnetic field strength signals representing the measured AC magnetic field strengths with the receiver coil;

(vi) measuring accelerometer data with the system accelerometer and generating accelerometer signals representing the accelerometer data;

(vii) transmitting the AC magnetic field strength signals and the accelerometer signals to the electronics module;

(viii) determining at least one anatomical displacement of the subject as a function of the AC magnetic field strength signals;

(ix) determining at least one respiratory parameter of the subject as a function of the determined anatomical displacement;

(x) determining a respiratory parameter value as a function of the AC magnetic field strength signals;

(xi) determining at least one respiratory disorder as a function of the determined respiratory parameter and value thereof; and (xii) determining at least one anatomical position of the subject as a function of the accelerometer signals.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
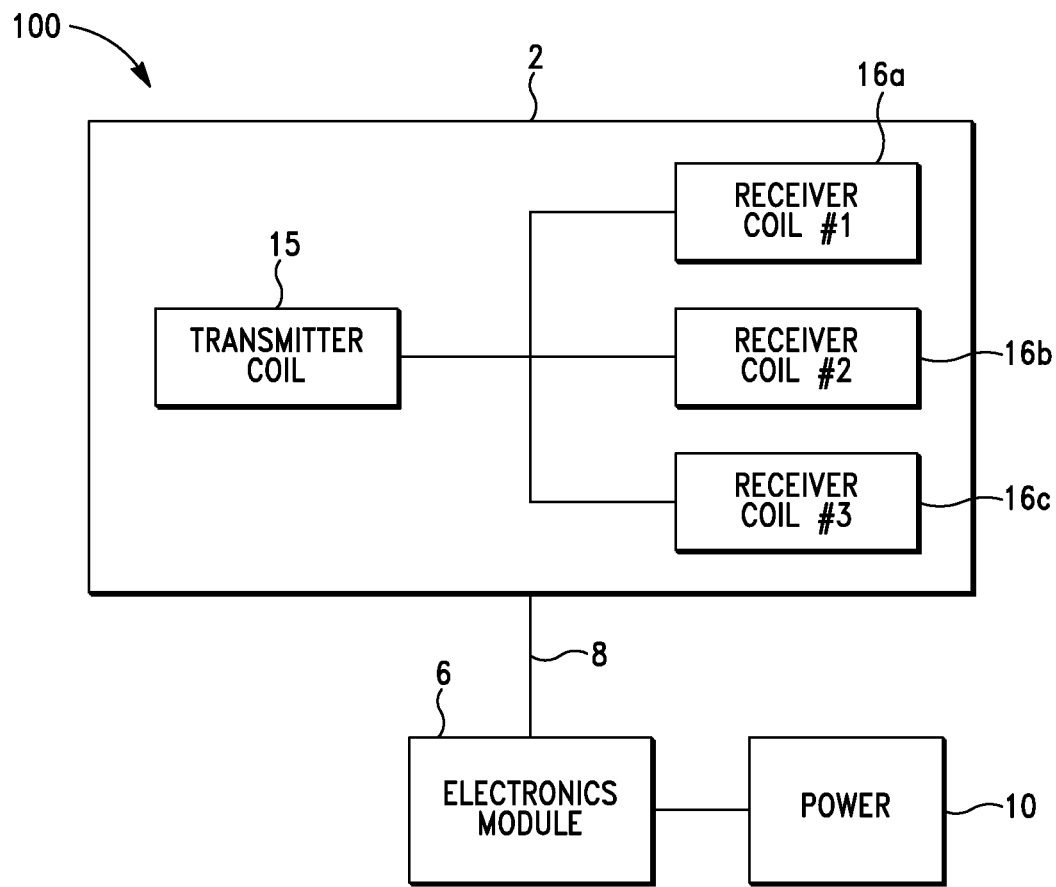
FIG. 1 is a schematic illustration of one embodiment of a physiological monitoring system, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a", "an" and "the" include plural referents unless the content clearly dictates otherwise. Thus, for example, reference to "an AC magnetic field strength signal" includes two or more such signals and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "respiratory parameter", "respiratory characteristic" and "respiration parameter" are used interchangeably herein, and mean and include a characteristic associated with the respiratory system and functioning thereof, including, without limitation, breathing frequency, tidal volume, inspiration volume, expiration volume, minute ventilation, inspiratory breathing time, expiratory breathing time, and flow rates (e.g., rates of change in the chest wall volume).

The terms "respiratory parameter", "respiratory characteristic" and "respiration parameter" further mean and include parameters associated with ventilation mechanics from synchronous or asynchronous movements of the chest wall compartments.

The terms "physiological parameter" and "physiological characteristic", as used herein, mean and include, without limitation, electrical activity of the heart, electrical activity of other muscles, electrical activity of the brain, pulse rate, blood pressure, blood oxygen saturation level, skin temperature, and core temperature.

The term "apnea," as used herein, means and includes abnormal respiration, as defined herein, of a subject, which is characterized by at least one respiratory parameter and/or physiological characteristic.

The term "apnea" thus means and includes abnormal respiration characterized by, without limitation, breathing frequency or respiratory rate (f) (e.g., breaths per minute), tidal volume ($V_T$), inspiration volume, expiration volume, respiratory minute ventilation (e.g., inspiration volume per minute or expiration volume per minute) and/or peak expiratory flow rate.

The term "apnea" thus means and includes the inability of a subject to correctly modulate respiration.

The term "apnea" also means and includes, without limitation, an obstruction of the subject's upper airway.

The term "apnea" further means and includes abnormal respiration characterized by, without limitation, a seminal blood oxygen parameter and/or blood oxygen characteristic including, without limitation, oxyhemoglobin saturation and oxygen desaturation index of a subject, e.g., oxyhemoglobin desaturation events per hour.

The term "apnea" thus means and includes, without limitation, a reduction of a subject's oxyhemoglobin saturation level ≥5% of the subject's average normal oxyhemoglobin saturation level.

The term "apnea" also means and includes, without limitation, counter-correlated contraction and expansion of the subject's thoracic and abdominal regions during at least one respiration cycle, i.e., the expansion and contraction of the subject's thoracic and abdominal cavities are ~180° out of phase.

The term "apnea" also means and includes central sleep apnea and obstructive sleep apnea.

The term "apnea" also means and includes complex sleep apnea or mixed sleep apnea, i.e., a combination of central and obstructive sleep apnea.

The term "apneic event," as used herein, means and includes, without limitation, a reduction of a subject's minute ventilation ≥30% of the subject's average normal minute ventilation and/or a cessation in the subject's breathing ≥10 seconds with an attendant reduction in oxyhemoglobin saturation.

The term "normal respiration" as used herein in connection with "apnea" means and includes, without limitation, a "normal" or "healthy" apnea/hypopnea index (AHI), i.e., an AHI score ≤5 apneic events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration," as used herein, means and includes, without limitation, cessation of a subject's breathing for a period ≥10 seconds with an attendant reduction in oxyhemoglobin saturation (or oxygen saturation).

The term "abnormal respiration" further means and includes, without limitation, a reduction of a subject's ventilation ≥30% of the subject's average normal ventilation.

The term "abnormal respiration" further means and includes, without limitation, a reduction of a subject's minute ventilation (V-dot)≥30% of the subject's average normal minute ventilation.

The term "abnormal respiration" further means and includes, without limitation, a "mild" apnea/hypopnea index (AHI) score in the range of 5-15 apneic events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration" further means and includes, without limitation, a "moderate" apnea/hypopnea index (AHI) score in the range of 15-30 events per hour of a subject's sleep, wherein an apneic event is defined as (i) a reduction of the subject's minute ventilation ≥30% of the subject's average normal minute ventilation and/or (ii) a cessation in the subject's breathing ≥10 seconds with an attendant reduction in oxyhemoglobin saturation.

The term "abnormal respiration" further means and includes, without limitation, a "severe" apnea/hypopnea index (AHI) score ≥30 events per hour of a subject's sleep, wherein an apneic event is defined as (i) a reduction of the subject's minute ventilation ≥30% of the subject's average normal minute ventilation and/or (ii) a cessation in the subject's breathing for a period of at least 10 seconds with an attendant reduction in oxyhemoglobin saturation.

The term "abnormal respiration" further means and includes, without limitation, a reduction of a subject's tidal volume ($V_T$) in the range of approximately 5-30% of the subject's average normal $V_T$.

The terms "sleep disorder" and "respiratory disorder" are used interchangeably herein, and mean and include, without limitation, an apnea, sleep apnea, hypopnea, and abnormal respiration.

The term "resting position" as used herein in connection with "apnea" and "sleep apnea" means and includes minimal physical activity or motion and/or the absence of physical activity or motion, except motion associated with normal breathing.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "subject" and "patient" also mean and include a wearer or user of a respiratory parameter monitoring system or a respiratory-physiological parameter monitoring system of the invention.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

Although the physiological monitoring systems and associated methods for determining respiratory and physiological parameters, and respiratory disorders based thereon, and anatomical positions and movement of a subject are described herein in connection with determining respiratory and physiological parameters, and respiratory and sleep disorders based thereon, and anatomical positions and movement of a human subject, it is understood that the invention is not limited to such use. Indeed, the physiological monitoring systems and associated methods can also be readily employed to determine respiratory and physiological parameters, and respiratory and sleep disorders based thereon, and anatomical positions and movement of other mammalian bodies.

The physiological monitoring systems and associated methods of the invention can also be employed in non-medical contexts, such as determining volumes and/or volume changes in extensible bladders used for containing liquids and/or gasses.

As indicated above, the present invention is directed to physiological monitoring systems and improved methods employing same for determining (i) respiratory and sleep disorders of a subject based on measured variations in AC magnetic field strengths that are detected and measured by a plurality of receiver coils as a function of the dimensional distances between each receiver coil and at least one magnetic field source, i.e., a transmitter coil, and, hence, anatomical displacements based thereon, and, in some embodiments, physiological parameters and/or characteristics, and accelerometer data, and/or (ii) anatomical positions and movement of the subject.

As discussed in detail below, in a preferred embodiment, the monitoring systems of the invention comprise a wearable garment that is configured to cover at least the chest region and upper back of a wearer (or user).

In some embodiments of the invention, the monitoring systems comprise a respiratory parameter monitoring sub-system, electronics (i.e., control and processing) module and integral signal transmission means associated therewith.

In some embodiments, the monitoring systems similarly comprises a respiratory parameter monitoring sub-system, a physiological parameter monitoring sub-system, electronics module and integral signal transmission means associated therewith.

In some embodiments of the invention, the respiratory parameter monitoring sub-system comprises at least one permanent magnet and at least one magnetometer, such as disclosed in Applicant's Co-pending U.S. application Ser. No. 16/363,290, which is incorporated by reference herein in its entirety.

In a preferred embodiment of the invention, the respiratory parameter monitoring sub-system comprises at least one transmitter coil and multiple receiver coils, such as disclosed in Applicant's Co-pending U.S. application Ser. No. 16/363,404, now U.S. Pat. No. 10,993,638, which is incorporated by reference herein in its entirety.

According to the invention, the respiratory parameter monitoring sub-system can comprise two (2) transmitter coils. As discussed in detail below, in such embodiments, one (1) transmitter coil is positioned proximate the xyphoid process and another transmitter coil is positioned proximate the umbilicus.

In a preferred embodiment of the invention, the respiratory parameter monitoring sub-system comprises three (3) receiver coils. According to the invention, the respiratory parameter monitoring sub-system can, however, also comprise more or less than three (3) receiver coils.

In a preferred embodiment of the invention, the transmitter coil(s) are adapted to generate and transmit electromagnetic radiation, e.g., AC magnetic fields, in three dimensions at multiple, non-harmonic frequencies.

In a preferred embodiment, the non-harmonic frequencies are less than 10 KHz.

In some embodiments, the non-harmonic frequencies are less than 5 KHz.

In some embodiments, the non-harmonic frequencies are in the range of approximately 5-10 KHz.

According to the invention, the transmitter coils can comprise any apparatus or system that is adapted to generate and transmit electromagnetic radiation at multiple frequencies.

In a preferred embodiment, the receiver coils are configured and positioned to detect and measure the field strength in at least one field dimension of at least one AC magnetic field at a defined frequency, and generate at least one AC magnetic field strength signal representing the field strengths in the detected field dimension of the AC magnetic field, and, thereby, anatomical displacements of the monitored subject.

More preferably, the receiver coils are configured and positioned to detect and measure the field strengths in multiple field dimensions of at least one AC magnetic field at a defined frequency, and generate a plurality of AC magnetic field strength signals representing the field strengths in the field dimensions of the AC magnetic field, and, thereby, anatomical displacements of the monitored subject.

According to the invention, the receiver coils can comprise any apparatus or system that is configured to detect and measure field strength in an AC magnetic field at a defined frequency, and generate at least one AC magnetic field strength signal representing the measured field strength in the AC magnetic field, such as a magnetometer or Hall effect sensor.

In a preferred embodiment of the invention, the transmitter coil is positioned at a first anatomical position proximate the subject's xyphoid process and a first receiver coil is positioned at a second anatomical position proximate the umbilicus, a second receiver coil is positioned at a third anatomical position proximate the subject's spine opposite the transmitter coil, and a third receiver coil is positioned at a fourth anatomical position proximate the subject's spine opposite the umbilicus.

According to the invention, other receiver placement configurations on a subject can be employed.

By way of example, in some embodiments of the invention, the transmitter coil is positioned proximate the subject's umbilicus and a first receiver coil is positioned proximate the subject's spine opposite the transmitter coil, a second receiver coil is positioned proximate the subject's xyphoid process, and a third receiver coil is positioned proximate the subject's spine opposite the xyphoid process.

In some embodiments of the invention, the transmitter coil is positioned proximate the subject's spine opposite the xyphoid process, and a first receiver coil is positioned proximate the xyphoid process, a second receiver coil is positioned proximate the subject's umbilicus, and a third receiver coil is positioned proximate the subject's spine opposite the umbilicus.

In a preferred embodiment of the invention, the physiological parameter monitoring sub-system comprises at least one physiological parameter sensor that is configured to (i) detect and measure a physiological parameter and, preferably, a value thereof, and (ii) generate a physiological parameter signal representing the measured physiological parameter and, preferably, value thereof.

In some embodiments, the physiological parameter monitoring sensor comprises a $SpO_2$ sensor.

In some embodiments, the physiological parameter monitoring sensor comprises a body temperature sensor.

In some embodiments of the invention, the physiological parameter monitoring sub-system further comprises at least one accelerometer that is configured and positioned to (i) detect anatomical positions of a monitored subject, and (ii) monitor physical movement of the subject.

In some embodiments, the accelerometer comprises a conventional three (3) axis accelerometer that is configured to detect at least one accelerometer parameter in an X, Y and/or Z direction.

According to the invention, the accelerometer is configured to generate and transmit at least one accelerometer signal representing accelerometer data, including at least one accelerometer parameter representing an anatomical position of a subject.

In a preferred embodiment, the accelerometer is configured and positioned to generate a plurality of accelerometer signals that are processed and employed to determine at least one anatomical position of the subject, i.e., whether the subject is in an erect, semi-erect, left lateral recumbent lying, right lateral recumbent lying, supine or prone position.

As indicated above, in a preferred embodiment, the electronics module comprises a multi-channel module that is programmed and configured (i.e., comprises programs, parameters, instructions and at least one algorithm) to control the monitoring systems of the invention.

In some embodiments of the invention, the electronics module is also preferably programmed and configured to (i) receive AC magnetic field strength signals that are generated and transmitted by the receiver coils, (ii) identify the frequency of each of the associated AC magnetic field strength signals, (iii) determine the identity and, thereby, position of the receiver coil based on the frequency of the AC magnetic field strength signals, (iv) determine at least one respiratory parameter, more preferably, a plurality of respiratory parameters associated with the monitored subject as a function of the AC magnetic field strength signals, (v) determine at least one respiratory parameter value as a function of the AC magnetic field strength signals, and (vi) determine at least one respiratory disorder as a function of the determined respiratory parameter and determined value thereof.

In some embodiments of the invention, the electronics module is further programmed and configured to (i) receive at least one respiratory parameter signal representing a pre-measured baseline respiratory parameter value, and (ii) determine at least one respiratory disorder as a function of the pre-measured baseline respiratory parameter value and the respiratory parameter and value thereof determined as a function of the AC magnetic field strength signals.

In some embodiments of the invention, the electronics module is further programmed and configured to receive and process physiological parameter signals representing physiological parameter values of a subject that are generated and transmitted by the physiological parameter monitoring sub-system, i.e., a physiological parameter sensor thereof.

Thus, in some embodiments, the electronics module is preferably programmed and configured to (i) receive the AC magnetic field strength signals that are transmitted by the receiver coils and physiological parameter signal(s) transmitted by the physiological parameter sensor, (ii) identify the frequency of each of the AC magnetic field strength signals, (iii) determine the identity of the receiver coil based on the frequency of the AC magnetic field strength signals, (iv) determine at least one respiratory parameter, more preferably, a plurality of respiratory parameters associated with the monitored subject as a function of the AC magnetic field strength signals, (v) determine at least one respiratory parameter value as a function of the AC magnetic field strength signals, and (vi) determine at least one respiratory disorder as a function of the physiological parameter value, and the respiratory parameter and value thereof determined as a function of the AC magnetic field strength signals.

In some embodiments, the electronics module is further programmed and configured to (i) receive accelerometer signals representing the anatomical position and movement data of the monitored subject that are generated and transmitted by an accelerometer, and (ii) determine at least one respiratory disorder as a function of the pre-measured baseline respiratory parameter value, physiological parameter value, accelerometer data, and the respiratory parameter and value thereof determined as a function of the AC magnetic field strength signals.

In some embodiments of the invention, the electronics module is also programmed to determine a physiological parameter value as a function of the physiological parameter signal.

In some embodiments of the invention, the electronics module is also programmed and configured to generate and transmit at least one respiratory disorder warning signal as a function of (or in response to) a pre-determined respiratory parameter threshold value and/or physiological parameter threshold value.

In some embodiments, the electronics module is further programmed and configured to generate and transmit at least one anatomical position warning signal as a function of (or in response to) a determined anatomical position and a pre-determined anatomical position of the subject.

In a preferred embodiment of the invention, the monitoring systems further comprise at least one excitation device, such as a vibration, audio or illuminating device, which generates or provides at least one excitation event, e.g., vibrations, in response to the respiratory disorder warning signal and/or anatomical position warning signal.

In some embodiments of the invention, the monitoring systems thus further comprise a vibration device that is configured to receive the respiratory disorder warning signal and/or anatomical position warning signal and generate vibrations at a pre-determined frequency or frequencies in response to the respiratory disorder warning signal and/or anatomical position warning signal.

According to the invention, the vibration device can comprise various conventional vibration devices, including, without limitation, piezoelectric vibrators, eccentric cam motors and electromagnetic (EM) vibrators.

In a preferred embodiment of the invention, the vibration device is capable of generating vibrations with a frequency in the range of approximately 5-50 Hz.

In some embodiments, the vibration device is configured to generate a plurality of vibrations in a series of random or continuous pulses in intervals in the range of 1-30 seconds, more preferably, in intervals in the range of 1-3 seconds.

In some embodiments of the invention, the monitoring systems further comprise a remote vibration device that is configured to receive the respiratory disorder warning signal and/or anatomical position warning signal and generate the vibrations referenced above in response to the respiratory disorder warning signal and/or anatomical position warning signal.

According to the invention, the remote vibration device can comprise various conventional vibration devices, including, without limitation, piezoelectric vibrators, eccentric cam motors and electromagnetic (EM) vibrators.

In a preferred embodiment of the invention, the remote vibration device is capable of vibrating at a frequency in the range of approximately 5-50 cycles per second (Hz).

In some embodiments, the remote vibration device is similarly configured to generate a plurality of vibrations in a series of random or continuous pulses in intervals in the range of 1-30 seconds, more preferably, in intervals in the range of 1-3 seconds.

According to the invention, the monitoring systems can comprise a plurality of vibration devices that are configured to generate and, hence, transmit the same or different vibrations.

In some embodiments, the monitoring systems comprise a vibration device that is in communication with a subject's bed, such as a bed frame or mattress, or chair.

In some embodiments of the invention, the monitoring systems further comprise an integral audio device that is configured to receive the respiratory disorder warning signal and/or anatomical position warning signal and produce an audible signal at a pre-determined amplitude in response to the respiratory disorder warning signal and/or anatomical position warning signal.

According to the invention, the integral audio device can comprise various conventional audio devices, including, without limitation, piezoelectric audio devices and electromagnetic audio devices, e.g., speakers.

In a preferred embodiment of the invention, the audio device is capable of providing an audible signal with an amplitude in the range of approximately 70-90 dB.

In a preferred embodiment of the invention, the audio device is capable of generating acoustic signals with a frequency in the range of approximately 300-1200 Hz.

In some embodiments of the invention, the monitoring systems further comprise a remote audio device that is configured to receive the respiratory disorder warning signal and/or anatomical position warning signal and produce an audible signal at a pre-determined amplitude in response to the respiratory disorder warning signal and/or anatomical position warning signal.

According to the invention, the remote audio device can similarly comprise various conventional audio devices, including, without limitation, piezoelectric audio devices and electromagnetic audio devices, e.g., speakers.

In a preferred embodiment of the invention, the remote audio device is capable of generating and transmitting an audible signal with an amplitude in the range of approximately 70-110 dB.

In a preferred embodiment of the invention, the remote audio device is capable of generating and transmitting acoustic signals with frequencies in the range of approximately 300-1200 Hz.

In some embodiments of the invention, the monitoring systems further comprise a remote illuminating device that is configured to receive the respiratory disorder warning signal and/or anatomical position warning signal and produce a luminous signal in response to the respiratory disorder warning signal and/or anatomical position warning signal.

According to the invention, the remote illuminating device can comprise any conventional device that is configured to generate light, such as a lamp or any local light source.

In some embodiments of the invention, electronics module of the monitoring systems is also programmed and configured to transmit a pre-programmed verbal notice or warning in response to the respiratory disorder warning signal and/or anatomical position warning signal.

In some embodiments of the invention, the electronics module is programmed and configured to transmit a pre-programmed respiratory disorder verbal warning to an emergency person or entity via a wireless link.

By way of example, in some embodiments, the electronics module is programmed to transmit the pre-programmed respiratory disorder verbal warning to an emergency contact via a pre-programmed telephone number.

In some embodiments, the electronics module is programmed to transmit the pre-programmed respiratory disorder verbal warning to an emergency service, e.g., police or fire department, via a pre-programmed emergency service telephone number, e.g., "911".

In a preferred embodiment of the invention, the electronics module is programmed and configured to provide a plurality of respiratory disorder warning signals and/or anatomical position warning signals that induce multi-level excitation or warning events, i.e., vibrations of the vibration device at different frequencies, induced audible signals at different amplitudes and verbal warnings to emergency contacts and/or services, and combinations thereof, as a function of (or in response to) the respiratory disorder warning signals and/or anatomical position warning signals.

Referring now to Table I, there is shown one embodiment of a single-level sleep disorder warning system of the invention. As illustrated in Table I, the single-level respiratory disorder warning system preferably comprises at least one respiratory-physiological parameter threshold and at least one excitation event relating thereto.

TABLE 1

| Alert Level | Respiratory-Physiological Parameter Threshold | Excitation Event |
| --- | --- | --- |
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |

Referring now to Table II, there is shown one embodiment of a two-level respiratory disorder warning system. As illustrated in Table II, the two-level respiratory disorder warning system, preferable comprises a plurality of respiratory-physiological parameter thresholds and at least one excitation event relating thereto.

TABLE II

| Alert Level | Respiratory-Physiological Parameter Threshold | Excitation Event |
| --- | --- | --- |
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |
| Level 2 | "Moderate" apnea/hypopnea index (AHI) score in the range of 15-30 apneic events per hour of a subject's sleep. | A series of ~5-50 Hz vibrations comprising at least 1 pulse every two (2) seconds; preferably, sufficient to fully wake a subject and/or an audible signal of at least 70 dB produced by an integral audio device and/or remote device that steadily increases amplitude to a maximum of 90 dB until the subject wakes or turns off the vibration device and/or audible signal. |

Referring now to Table III, there is shown one embodiment of a three-level respiratory disorder warning system. As illustrated in Table III, the three-level sleep disorder warning system similarly preferably comprises a plurality of respiratory-physiological parameter thresholds and at least one excitation event relating thereto.

TABLE III

| Alert Level | Respiratory-Physiological Parameter Threshold | Excitation Event |
| --- | --- | --- |
| Level 1 | "Mild" apnea/hypopnea index (AHI) score in the range of 5-15 apneic events per hour of a subject's sleep. | A series of ~5-50 Hz vibrations comprising at least 1-3 pulses per second; preferably, sufficient to fully wake a subject. The vibrations transmitted until the subject wakes or turns off the vibration device. |
| Level 2 | "Moderate" apnea/hypopnea index (AHI) score in the range of 15-30 apneic events per hour of a subject's sleep. | A series of ~5-50 Hz vibrations comprising at least 1 pulse every two (2) seconds; preferably, sufficient to fully wake a subject and/or an audible signal of at least 70 dB produced by an integral audio device and/or remote device that steadily increases amplitude to a maximum of 90 dB until the subject wakes or turns off the vibration device and/or audible signal. |
| Level 3 | "Severe" apnea/hypopnea index (AHI) score >30 apneic events per hour of a subject's sleep. | Transmittal of a verbal warning to an emergency contact and/or service, e.g., 911. |

As indicated above, in a preferred embodiment, the accelerometer is configured and positioned to (i) detect and monitor anatomical positions and movements of the monitored subject, and (ii) generate a plurality of accelerometer signals that are processed and employed by the electronics module to determine anatomical positions of the subject.

As also indicated above, in some embodiments, the electronics module is also programmed and configured to generate and transmit at least one anatomical position warning signal as a function of (or in response to) a determined anatomical position and a pre-determined anatomical position of the subject.

In a preferred embodiment of the invention, the pre-determined and determined anatomical positions include at least semi-erect, left lateral recumbent, right lateral recumbent, supine and prone positions.

In a preferred embodiment, the anatomical position warning signal induces excitation or warning events that are configured to prompt a subject to transition to an alternate anatomical position that is less likely to exacerbate and/or trigger a symptom of an existing respiratory or sleep disorder of the subject, e.g., obstructive sleep apnea or gastroesophageal reflux disease.

Referring now to Table IV, there is shown one embodiment of a single-level anatomical position warning system of the invention. As illustrated in Table IV, the single-level anatomical position warning system preferably comprises at least one undesirable anatomical position or condition and at least one excitation event relating thereto.

TABLE IV

| Anatomical Condition | Excitation Event |
| --- | --- |
| Subject sleeping in a supine position. | A series of ~5-50 Hz vibrations comprising at least 1-3 pulses per second; preferably, sufficient to prompt a subject to transition to a left lateral recumbent lying position. The vibrations transmitted until the subject transitions to a left lateral recumbent lying position, wakes or turns off the vibration device. |

Referring now to Table V, there is shown another embodiment of a single-level anatomical position warning system of the invention. The illustrated embodiment similarly comprises at least one undesirable anatomical position or condition and at least one excitation event relating thereto.

TABLE V

| Anatomical Condition | Excitation Event |
| --- | --- |
| Subject sleeping in a supine position. | A series of ~5-50 Hz vibrations comprising at least 1 pulse every two (2) seconds until the subject transitions to a left lateral recumbent lying position, wakes or turns off the vibration device and/or an audible signal of at least 70 dB produced by an integral audio device and/or remote device that steadily increases amplitude to a maximum of 90 dB until the subject transitions to a left lateral recumbent lying position, wakes or turns off the audible device. |

Referring now to Table VI, there is shown another embodiment of a single-level anatomical position warning system of the invention.

TABLE VI

| Anatomical Condition | Excitation Event |
| --- | --- |
| Subject sleeping in a prone position. | A series of ~5-50 Hz vibrations comprising at least 1 pulse every two (2) seconds until the subject transitions to a left lateral recumbent lying position, wakes |

TABLE VI-continued

| Anatomical Condition | Excitation Event |
| --- | --- |
| | or turns off the vibration device and/or an audible signal of at least 70 dB produced by an integral audio device and/or remote device that steadily increases amplitude to a maximum of 90 dB until the subject transitions to a left lateral recumbent lying position, wakes or turns off the audible device. |

In a preferred embodiment of the invention, the anatomical position warning system is thus configured to train a subject to maintain an anatomical position during sleep that is less likely to exacerbate and/or trigger a symptom of an existing respiratory or sleep disorder of the subject.

In some embodiments of the invention, the anatomical position warning system is specifically configured to continuously train a subject afflicted with obstructive sleep apnea to maintain a left or right lateral recumbent lying anatomical position during sleep.

In some embodiments, the anatomical position warning system is specifically configured to continuously train a subject afflicted with gastroesophageal reflux disease to maintain a left lateral recumbent lying anatomical position during sleep.

According to the invention, the anatomical position warning system can be configured to train a subject to maintain an anatomical position during sleep that is less likely to exacerbate and/or trigger a symptom of any existing disorder or disease of a subject.

In some embodiments of the invention, the electronics module is further programmed and configured to continuously monitor the frequency of a subject's anatomical position transition events.

In some embodiments, electronics module is also programmed and configured to determine sleep parameters, e.g., total sleep time (TST), sleep efficiency (SE) and wake-after-sleep-onset (WASO), as a function of acquired accelerometer data and determined respiratory parameter values.

Thus, as set forth in detail in priority U.S. application Ser. No. 16/363,404, now U.S. Pat. No. 10,993,638, in one embodiment of the invention the monitoring systems generally comprise a wearable garment that is configured to be removably positioned on a subject, the subject comprising thoracic and abdominal regions, a spine, an umbilicus and xyphoid process of the sternum, wherein when the wearable garment is positioned on a subject the wearable garment covers at least the thoracic and abdominal regions of the subject, the wearable garment comprising a respiratory parameter monitoring sub-system and an electronics module in communication therewith, the respiratory parameter monitoring sub-system comprising a transmitter coil and first, second and third receiver coils, the transmitter coil and the first, second and third receiver coils being positioned on the wearable garment, whereby, when the wearable garment is positioned on the subject, the transmitter coil is positioned proximate the subject's xyphoid process, the first receiver coil is positioned at a first anatomical region of the subject proximate the subject's umbilicus at a first receiver coil distance from the transmitter coil, the second receiver coil is positioned at a second anatomical region of the subject proximate the subject's spine opposite the subject's xyphoid process at a second receiver coil distance from the transmitter coil, the third receiver coil is positioned at a third anatomical region of the subject proximate the subject's spine opposite the subject's umbilicus at a third receiver coil distance from the transmitter coil, the transmitter coil being adapted to generate a first alternating current (AC) magnetic field in first, second and third field dimensions, a second AC magnetic field in fourth, fifth and sixth field dimensions, and a third AC magnetic field in seventh, eighth and ninth field dimensions, the first, second and third field dimensions of the first AC magnetic field comprising a first field frequency, the fourth, fifth and sixth field dimensions of the second AC magnetic field comprising a second field frequency, and the seventh, eighth and ninth field dimensions of the third AC magnetic field comprising a third field frequency, the first field dimension of the first AC magnetic field comprising a first variable strength as a function of a first distance of the first receiver coil from the transmitter coil, the second field dimension of the first AC magnetic field comprising a second variable strength as a function of a second distance of the first receiver coil from the transmitter coil, and the third field dimension of the first AC magnetic field dimension comprising a third variable strength as a function of a third distance of the first receiver coil from the transmitter coil, the fourth field dimension of the second AC magnetic field comprising a fourth variable field strength as a function of a fourth distance of the second receiver coil from the transmitter coil, the fifth field dimension of the second AC magnetic field comprising a fifth variable field strength as a function of a fifth distance of the second receiver coil from the transmitter coil, and the sixth field dimension of the second AC magnetic field comprising a sixth variable field strength as a function of a sixth distance of the second receiver coil from the transmitter coil, the seventh field dimension of the third AC magnetic field comprising a seventh variable field strength as a function of a seventh distance of the third receiver coil from the transmitter coil, the eighth field dimension of the third AC magnetic field comprising an eighth variable field strength as a function of an eighth distance of the third receiver coil from the transmitter coil, and the ninth field dimension of the third AC magnetic field comprising a ninth variable field strength as a function of a ninth distance of the third receiver coil from the transmitter coil, the first receiver coil being configured to detect and measure the first, second and third variable field strengths in the first, second and third field dimensions of the first AC magnetic field, the first receiver coil being further configured to generate a first AC magnetic field strength signal representing the first variable field strength in the first field dimension of the first AC magnetic field, a second AC magnetic field strength signal representing the second variable field strength in the second field dimension of the first AC magnetic field, and a third AC magnetic field strength signal representing the third variable field strength in the third field dimension of the first AC magnetic field, and transmit the first, second and third AC magnetic field strength signals to the electronics module, the second receiver coil being configured to detect and measure the fourth, fifth and sixth variable field strengths in the fourth, fifth and sixth field dimensions of the second AC magnetic field, the second receiver coil being further configured to generate a fourth AC magnetic field strength signal representing the fourth variable field strength in the fourth field dimension of the second AC magnetic field, a fifth AC magnetic field strength signal representing the fifth variable field strength in the fifth field dimension of the second AC magnetic field, and a sixth AC magnetic field strength signal representing the sixth variable field strength in the sixth field dimension of the second AC magnetic field, and transmit the fourth, fifth and sixth AC magnetic field strength signals to the electronics module, the third receiver coil being configured to detect and measure the seventh, eighth and ninth variable field strengths in the seventh, eighth and ninth field dimensions of the third AC magnetic field, the third receiver coil being further configured to generate a seventh AC magnetic field strength signal representing the seventh variable field strength in the seventh field dimension of the third AC magnetic field, an eighth AC magnetic field strength signal representing the eighth variable field strength in the eighth field dimension of the third AC magnetic field, and a ninth AC magnetic field strength signal representing the ninth variable field strength in the ninth field dimension of the third AC magnetic field, and transmit the seventh, eighth and ninth AC magnetic field strength signals to the electronics module, the electronics module being adapted to receive the first, second and third AC magnetic field strength signals transmitted by the first receiver coil, the fourth, fifth and sixth AC magnetic field strength signals transmitted by the second receiver coil and the seventh, eighth and ninth AC magnetic field strength signals transmitted by the third receiver coil, the electronics module comprising a processing system that is programmed and configured to determine at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine at least one respiratory disorder of the subject as a function of the determined at least one respiratory parameter and said determined value thereof.

In some embodiments of the invention, wherein a baseline respiratory parameter value is pre-measured, the processing system is further programmed and configured to determine at least one respiratory or sleep disorder of the subject as a function of the pre-measured baseline respiratory parameter value and the determined at least one respiratory parameter and value thereof.

In a preferred embodiment of the invention, the transmitter coil and the first receiver coil are in a first axial alignment, the transmitter coil and the second receiver coil are in a second axial alignment and the transmitter coil and the third receiver coil are in a third axial alignment.

As also set forth in detail in priority U.S. application Ser. No. 16/363,404, in another embodiment of the invention the monitoring systems similarly comprise a wearable garment that is configured to be removably positioned on a subject, the subject comprising a spine, an umbilicus and xyphoid process of the sternum, wherein when the wearable garment is positioned on a subject the wearable garment covers at least a thoracic and abdominal region of the subject, the wearable garment comprising a respiratory parameter monitoring sub-system, physiological parameter sub-system and an electronics module, the respiratory parameter monitoring sub-system comprising a transmitter coil and first, second and third receiver coils, the physiological parameter sub-system comprising at least one physiological parameter sensor, the transmitter coil and the first, second and third receiver coils being positioned on the wearable garment, whereby, when the wearable garment is positioned on the subject, the transmitter coil is positioned proximate the subject's xyphoid process, the first receiver coil is positioned at a first anatomical region of the subject proximate the subject's umbilicus at a first receiver coil distance from the transmitter coil, the second receiver coil is positioned at a second anatomical region of the subject proximate the subject's spine opposite the subject's xyphoid process at a second receiver coil distance from the transmitter coil, the third receiver coil is positioned at a third anatomical region of the subject proximate the subject's spine opposite the subject's umbilicus at a third receiver coil distance from the transmitter coil, the transmitter coil being adapted to generate a first alternating current (AC) magnetic field in first, second and third field dimensions, a second AC magnetic field in fourth, fifth and sixth field dimensions, and a third AC magnetic field in seventh, eighth and ninth field dimensions, the first, second and third field dimensions of the first AC magnetic field comprising a first field frequency, the fourth, fifth and sixth field dimensions of the second AC magnetic field comprising a second field frequency, and the seventh, eighth and ninth field dimensions of the third AC magnetic field comprising a third field frequency, the first field dimension of the first AC magnetic field comprising a first variable strength as a function of a first distance of the first receiver coil from the transmitter coil, the second field dimension of the first AC magnetic field comprising a second variable strength as a function of a second distance of the first receiver coil from the transmitter coil, and the third field dimension of the first AC magnetic field dimension comprising a third variable strength as a function of a third distance of the first receiver coil from the transmitter coil, the fourth field dimension of the second AC magnetic field comprising a fourth variable field strength as a function of a fourth distance of the second receiver coil from the transmitter coil, the fifth field dimension of the second AC magnetic field comprising a fifth variable field strength as a function of a fifth distance of the second receiver coil from the transmitter coil, and the sixth field dimension of the second AC magnetic field comprising a sixth variable field strength as a function of a sixth distance of the second receiver coil from the transmitter coil, the seventh field dimension of the third AC magnetic field comprising a seventh variable field strength as a function of a seventh distance of the third receiver coil from the transmitter coil, the eighth field dimension of the third AC magnetic field comprising an eighth variable field strength as a function of an eighth distance of the third receiver coil from the transmitter coil, and the ninth field dimension of the third AC magnetic field comprising a ninth variable field strength as a function of a ninth distance of the third receiver coil from the transmitter coil, the first receiver coil being configured to detect and measure the first, second and third variable field strengths in the first, second and third field dimensions of the first AC magnetic field, the first receiver coil being further configured to generate a first AC magnetic field strength signal representing the first variable field strength in the first field dimension of the first AC magnetic field, a second AC magnetic field strength signal representing the second variable field strength in the second field dimension of the first AC magnetic field, and a third AC magnetic field strength signal representing the third variable field strength in the third field dimension of the first AC magnetic field, and transmit the first, second and third AC magnetic field strength signals to the electronics module, the second receiver coil being configured to detect and measure the fourth, fifth and sixth variable field strengths in the fourth, fifth and sixth field dimensions of the second AC magnetic field, the second receiver coil being further configured to generate a fourth AC magnetic field strength signal representing the fourth variable field strength in the fourth field dimension of the second AC magnetic field, a fifth AC magnetic field strength signal representing the fifth variable field strength in the fifth field dimension of the second AC magnetic field, and a sixth AC magnetic field strength signal representing the sixth variable field strength in the sixth field dimension of the second AC magnetic field, and transmit the fourth, fifth and sixth AC magnetic field strength signals to the electronics module, the third receiver coil being configured to detect and measure the seventh, eighth and ninth variable field strengths in the seventh, eighth and ninth field dimensions of the third AC magnetic field, the third receiver coil being further configured to generate a seventh AC magnetic field strength signal representing the seventh variable field strength in the seventh field dimension of the third AC magnetic field, an eighth AC magnetic field strength signal representing the eighth variable field strength in the eighth field dimension of the third AC magnetic field, and a ninth AC magnetic field strength signal representing the ninth variable field strength in the ninth field dimension of the third AC magnetic field, and transmit the seventh, eighth and ninth AC magnetic field strength signals to the electronics module, the electronics module being adapted to receive the first, second and third AC magnetic field strength signals transmitted by the first receiver coil, the fourth, fifth and sixth AC magnetic field strength signals transmitted by the second receiver coil and the seventh, eighth and ninth AC magnetic field strength signals transmitted by the third receiver coil, the electronics module comprising a processing system that is programmed and configured to determine at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine a value of the at least one respiratory parameter of the subject as a function of the first, second, third, fourth, fifth, sixth, seventh, eighth and ninth AC magnetic field strength signals, the processing system being further programmed and configured to determine at least one respiratory disorder of the subject as a function of the physiological parameter value, and the determined at least one respiratory parameter and the determined value thereof.

In a preferred embodiment of the invention, the transmitter coil and the first receiver coil are similarly in a first axial alignment, the transmitter coil and the second receiver coil are in a second axial alignment and the transmitter coil and the third receiver coil are in a third axial alignment.

In some embodiments of the invention, wherein a baseline respiratory parameter value is pre-measured, the processing system is further programmed and configured to determine at least one respiratory disorder of the subject as a function of the pre-measured baseline respiratory parameter value, physiological parameter value, and the determined at least one respiratory parameter and value thereof.

As also set forth in priority U.S. application Ser. No. 16/363,404 and discussed in detail above, in some embodiments of the invention, the physiological parameter sub-system of the monitoring systems of the invention further comprise an accelerometer that is configured detect and monitor anatomical positions and physical movement of the subject, and generate and transmit accelerometer signals representing same, including accelerometer data representing at least one anatomical position of the subject.

Thus, in some embodiments of the invention, the processing system is further programmed and configured to determine at least one respiratory disorder of the subject as a function of the pre-measured baseline respiratory parameter value, physiological parameter value, accelerometer data, and the determined at least one respiratory parameter and value thereof.

In some embodiments of the invention, the processing system is also programmed and configured to determine at least one anatomical position of the subject as a function of the accelerometer signals and, hence, accelerometer data embodied in same.

In some embodiments of the invention, the processing system is further programmed and configured to selectively determine at least one respiratory disorder of the subject as a function of the physiological parameter value and the determined at least one respiratory parameter and value thereof or at least one anatomical position of the subject as a function of the accelerometer signals and, hence, accelerometer data embodied in same.

As also set forth in priority U.S. application Ser. No. 16/363,404, in some embodiments of the invention, the method for determining a respiratory disorder with a monitoring system of the invention generally comprises:

(i) providing a wearable monitoring system comprising a respiratory parameter monitoring sub-system, physiological parameter monitoring sub-system and electronics control-processing module, the respiratory parameter monitoring sub-system comprising one transmitter coil and three, i.e., first, second and third, receiver coils, the physiological parameter monitoring sub-system comprising at least one physiological parameter monitoring sensor;

(ii) positioning the monitoring system on the subject, wherein the transmitter coil is positioned proximate the subject's xyphoid process and the first receiver coil is positioned proximate the umbilicus, the second receiver coil is positioned proximate the subject's spine opposite the transmitter coil, and the third receiver coil is positioned proximate the subject's spine opposite the umbilicus, and wherein the physiological parameter monitoring sensor is positioned proximate a target physical structure, e.g., the subject's skin;

(iii) initiating the monitoring system, wherein AC magnetic fields are generated and transmitted by the transmitter coil, the AC magnetic fields comprising predetermined frequencies;

(iv) generating and transmitting AC magnetic fields with the transmitter coil, the AC magnetic fields comprising predetermined frequencies;

(v) detecting and measuring strengths in the AC magnetic fields with the receiver coils;

(vi) generating AC magnetic field strength signals representing the measured AC magnetic field strengths with the receiver coils;

(vii) measuring at least one physiological parameter and value thereof with the physiological parameter monitoring sub-system and generating a physiological parameter signal representing the physiological parameter and value thereof;

(viii) transmitting the AC magnetic field strength signals and the physiological signal to the electronics module;

(ix) determining at least one anatomical displacement of the subject as a function of the AC magnetic field strength signals with the electronics module;

(x) determining at least one respiratory parameter of the subject as a function of the determined anatomical displacement with the electronics module;

(xi) determining a respiratory parameter value as a function of the AC magnetic field strength signals with the electronics module; and (xii) determining at least one respiratory disorder as a function of the physiological parameter value, and determined respiratory parameter and value thereof with the electronics module.

In some embodiments of the invention, the method for determining a respiratory disorder and anatomical position of a subject generally comprises:

(i) providing a wearable monitoring system comprising a respiratory parameter monitoring sub-system and electronics control-processing module, the respiratory parameter monitoring sub-system comprising one transmitter coil and first, second and third, receiver coils, the respiratory parameter monitoring sub-system comprising at least one physiological parameter monitoring sensor and an accelerometer;

(ii) positioning the monitoring system on the subject, wherein the transmitter coil is positioned proximate the subject's xyphoid process and the first receiver coil is positioned proximate the umbilicus, the second receiver coil is positioned proximate the subject's spine opposite the transmitter coil, and the third receiver coil is positioned proximate the subject's spine opposite the umbilicus, and wherein the physiological parameter monitoring sensor is positioned proximate a target physical structure, e.g., the subject's skin;

(iii) initiating the monitoring system, wherein AC magnetic fields are generated and transmitted by the transmitter coil, the AC magnetic fields comprising predetermined frequencies;

(iv) detecting and measuring strengths in the AC magnetic fields with the receiver coils;

(v) generating AC magnetic field strength signals representing the measured AC magnetic field strengths with the receiver coils;

(vi) acquiring accelerometer data with the accelerometer and generating accelerometer signals representing the accelerometer data, the accelerometer data including accelerometer parameters representing anatomical positions and movement of the subject;

(vii) transmitting the AC magnetic field strength signals and the accelerometer signals to the electronics module;

(viii) determining at least one anatomical displacement of the subject as a function of the AC magnetic field strength signals with the electronics module;

(ix) determining at least one respiratory parameter of the subject as a function of the determined anatomical displacement with the electronics module;

(x) determining a respiratory parameter value as a function of the AC magnetic field strength signals with the electronics module;

(xi) determining at least one respiratory disorder as a function of the acquired baseline accelerometer data and the determined respiratory parameter and value thereof with the electronics module; and (xii) determining at least one anatomical position of the subject as a function of the accelerometer signals with the electronics module.

Referring now to FIG. 1, there is shown a schematic illustration of one embodiment of a monitoring system of the invention. As illustrated in FIG. 1, the monitoring system 100 preferably comprises a respiratory parameter monitoring sub-system 2 of the invention, an electronics module 6 and signal transmission conductors 8.

As also illustrated in FIG. 1, the respiratory parameter monitoring sub-system 2 comprises a transmitter coil 15, first, second and third receiver coils 16a, 16b, 16c.

As further illustrated in FIG. 1, the respiratory parameter monitoring system 100 further comprises a power source 10. According to the invention, the power source 10 can comprise any device or system configured to provide (or generate) electrical energy, such as a battery.

In a preferred embodiment of the invention, the monitoring system 100 preferably comprises a wearable garment that is configured to cover at least a portion of the torso of a subject, i.e., the thoracic and abdominal regions.

Figure 2:
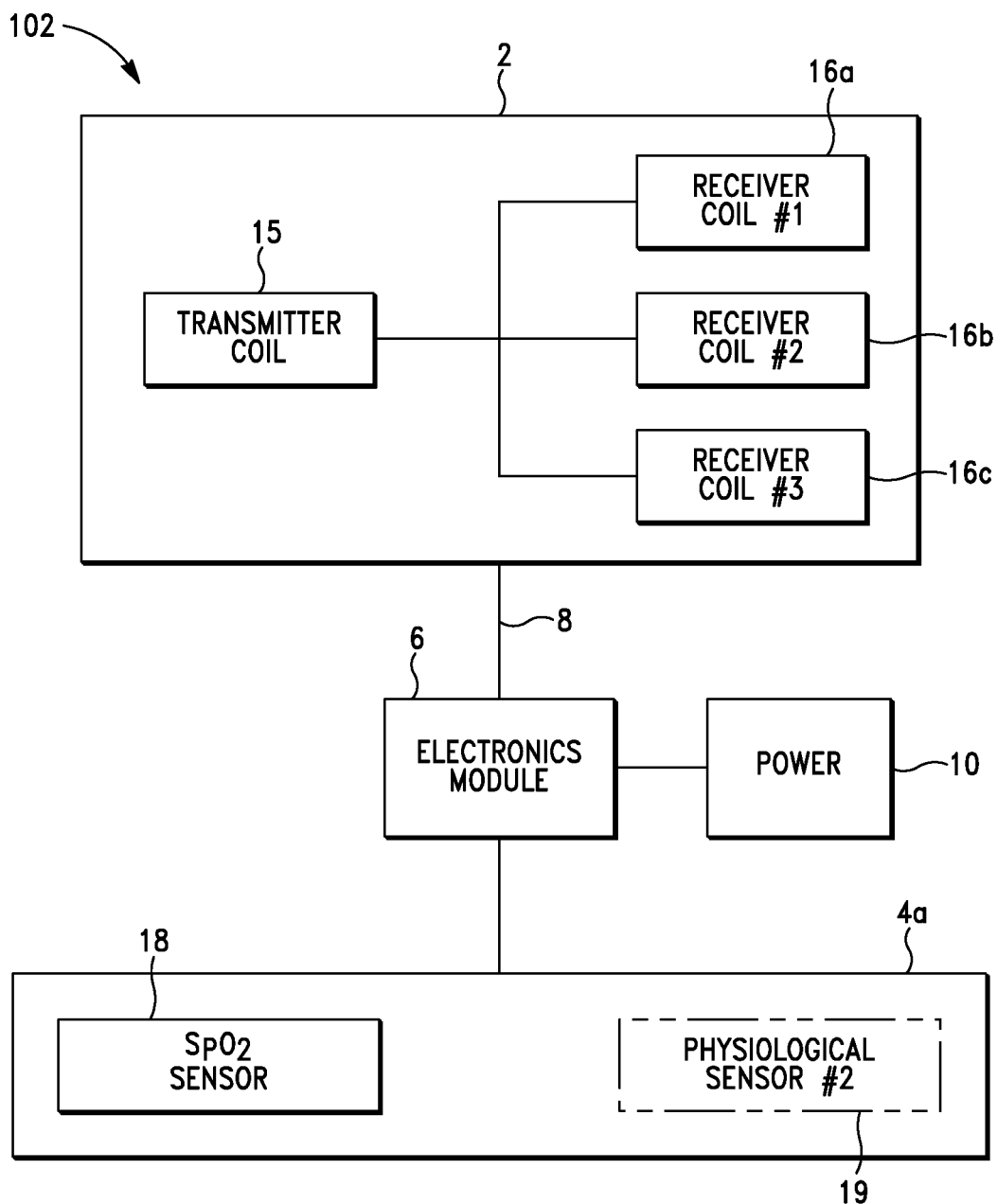
FIG. 2 is a schematic illustration of another embodiment of a physiological monitoring system, in accordance with the invention.

Referring now to FIG. 2, there is shown a schematic illustration of another embodiment of a monitoring system of the invention. As illustrated in FIG. 2, the monitoring system 102 similarly preferably comprises a respiratory parameter monitoring sub-system 2, an electronics module 6 and signal transmission conductors 8.

As also illustrated in FIG. 2, the respiratory parameter monitoring sub-system 2 similarly comprises a transmitter coil 15, first, second and third receiver coils 16a, 16b, 16c.

As further illustrated in FIG. 2, the monitoring system 102 further comprises a physiological parameter monitoring sub-system 4a of the invention.

In a preferred embodiment of the invention, the monitoring system 102 similarly preferably comprises a wearable garment that is configured to cover at least a portion of the torso of a subject, i.e., the thoracic and abdominal regions.

As indicated above, in a preferred embodiment of the invention, transmitter coil 15 is adapted to generate and transmit electromagnetic radiation, e.g., AC magnetic fields, in multiple fields, i.e., a three-dimensional field, at multiple, non-harmonic frequencies.

As indicated above, preferably the non-harmonic frequencies are less than 10 KHz.

As also indicated above, in a preferred embodiment, the first, second and third receiver coils 16a, 16b and 16c are configured and positioned to detect and measure field strength in at least one of the field dimensions of the AC magnetic fields and generate AC magnetic field strength signals representing the field strengths in the AC magnetic fields, and, thereby, anatomical displacements of the monitored subject.

In at least one embodiment, the first and second transmitter coils are configured and positioned on a subject, wherein the polarities of the AC magnetic fields generated by the transmitter coils that are oriented perpendicular to each other, i.e., at a 90° angle relative to each other, wherein a net vector field, comprising at least X and Y vectors (or directions), of the AC magnetic fields is provided.

In a preferred embodiment of the invention, at least one receiver coil is configured to detect at least one AC magnetic field vector in the X-direction and at least one receiver coil is configured to detect at least one AC magnetic field vector in the Y-direction.

In the noted embodiments of the invention, wherein two (2) transmitter coils are employed, when the AC magnetic field vectors in the X and Y directions are detected by the receiver coils, an angle between the X and Y AC magnetic field vectors and a net AC magnetic field vector based thereon is determined by the processing system of an electronics module. The angle between the X and Y AC magnetic field vectors and the net AC magnetic field vector are then used to determine at least one net AC magnetic field strength vector.

As indicated above and illustrated in FIG. 2, in a preferred embodiment of the invention, the physiological parameter monitoring sub-system 4a of the respiratory-physiological parameter monitoring system 102 comprises at least one physiological parameter monitoring sensor.

As further illustrated in FIG. 2, in some embodiments, the physiological parameter monitoring sensor 4a preferably comprises a $SpO_2$ sensor 18.

In some embodiments of the invention, the physiological parameter monitoring sub-system 4a comprises at least one additional physiological parameter monitoring sensor, such as a temperature sensor (shown in phantom and denoted 19).

In a preferred embodiment of the invention, the electronics module 6 preferably comprises a processing system or module, which is programmed and configured to control the respiratory-physiological parameter monitoring system 2 and the function thereof, and a data transmission module, which is programmed and configured to control the transmission and receipt of signals to and from the respiratory parameter monitoring sub-system 2 and physiological parameter monitoring sub-system 4a.

As indicated above, in a preferred embodiment of the invention, the processing system comprises at least one algorithm that is programmed and configured to isolate and process the AC magnetic field strength signals and determine at least one respiratory parameter (or characteristic) of a subject as a function of the AC magnetic field strength signals.

As set forth in priority U.S. application Ser. No. 16/363,404, the processing system algorithm for determining a respiratory parameter (or characteristic) as a function of AC magnetic field strength signals can comprise various conventional algorithms, including, without limitation, a conventional and/or modified multiple-degree of freedom algorithm, including, without limitation, a two (2) degree of freedom algorithm and three (3) degree of freedom algorithm, a spectral density estimation algorithm using non-parametric methods, including, without limitation, singular spectrum analysis, short-time Fourier transform, cross-power method, transfer function estimate and magnitude squared coherence, and frequency domain algorithm, including, without limitation, a Fourier series algorithm, Fourier transform algorithm, Laplace transform algorithm, Z transform algorithm and wavelet transform algorithm.

As also set forth in priority U.S. application Ser. No. 16/363,404, the processing system is also preferably programmed and configured to generate and continuously update at least one diagnostic data set. Preferably, the diagnostic data set correlates at least one array of measured or determined respiratory parameters with at least one array of measured or determined anatomical displacement parameters of a subject.

Referring now to Table VII, there is shown an illustration of one embodiment of a diagnostic data set for a subject. As illustrated in Table VII, the diagnostic data set preferably comprises at least an array of measured or determined minute ventilation values and anatomical displacements measured at defined points on a subject during monitoring with a respiratory parameter or respiratory-physiological parameter monitoring system of the invention.

TABLE VII

Subject #1

| Point No. | Minute Ventilation (V-dot) | Anatomical Displacement ($V_{M1}$, $V_{M2}$) |
|---|---|---|
| 0 | $V\text{-dot}_0$ | $(V_{M1}, V_{M2})_0$ |
| 1 | $V\text{-dot}_1$ | $(V_{M1}, V_{M2})_1$ |
| 2 | $V\text{-dot}_2$ | $(V_{M1}, V_{M2})_2$ |
| 3 | $V\text{-dot}_3$ | $(V_{M1}, V_{M2})_3$ |
| 4 | $V\text{-dot}_4$ | $(V_{M1}, V_{M2})_4$ |
| 5 | $V\text{-dot}_5$ | $(V_{M1}, V_{M2})_5$ |
| 6 | $V\text{-dot}_6$ | $(V_{M1}, V_{M2})_6$ |

According to the invention, the diagnostic data set shown in Table VII can be graphically presented, i.e., minute ventilation on the y-axis and anatomical displacement on the x-axis, and linearly interpolated using conventional equations, such as Eq. 1 shown below.

$$y = y_1 + (x - x_1)\frac{y_2 - y_1}{x_2 - x_1}$$

In a preferred embodiment, the processing system is programmed and configured to linearly interpolate a diagnostic data set, such as the diagnostic data set shown in Table VII, and determine the presence of at least one apneic event exhibited by a subject over a predetermined period of time and, thereby, a sleep disorder.

According to the invention, the diagnostic data set can be interpolated using any applicable methods and/or equations. In some embodiments, processing system is programmed and configured to interpolate a diagnostic data set using quadratic polynomial interpolation and determine the presence of at least one apneic event exhibited by a subject over a predetermined period of time and, thereby, a sleep disorder.

In some embodiments of the invention, a subject's tidal volume ($V_T$) and respiratory rate (f) are determined via spirometry. Minute ventilation (V-dot) can then be determined using the equation shown below.

$$V\text{-}dot = V_T \times f \qquad \text{Eq. 2}$$

In a preferred embodiment of the invention, the processing system is further programmed to differentiate between indicia of a sleep disorder, i.e., respiratory and/or physiological parameters indicative of a sleep disorder, and extraneous respiratory events, such as coughing, hiccups, sneezing, etc. by, for example, comparing the pre-measured baseline respiratory and pre-measured baseline physiological parameters of the subject in a resting position to predetermined respiratory and physiological parameter threshold values reflecting a respiratory disorder.

In a preferred embodiment of the invention, the processing system is further programmed to determine a type of sleep apnea, i.e., obstructive sleep apnea, central sleep apnea and complex sleep apnea, based on detected anatomical displacements of a monitored subject.

In some embodiments, the processing system determines the type of sleep apnea of a subject based on the correlation or synchrony between the expansion and contraction of the subject's thoracic and abdominal regions (or chest wall and abdominal wall) during at least one respiratory cycle.

As is well established, when a subject is afflicted with obstructive sleep apnea, the subject will exhibit a counter-correlated expansion and contraction of the thoracic and abdominal regions, i.e., the expansion and contraction of the thoracic and abdominal regions are ~180° out of phase, during at least one respiratory cycle.

As is also well established, when a subject is afflicted with central sleep apnea, the subject will exhibit a complete absence of thoracic and abdominal region expansion and contraction.

Thus, according to the invention, when the AC magnetic field strength signals reflect counter-correlated expansion and contraction of a subject's thoracic and abdominal regions during at least one respiratory cycle, a determination of obstructive sleep apnea is provided.

When the AC magnetic field strength signals reflect the absence of thoracic and abdominal region expansion and contraction, a determination of central sleep apnea is provided.

In a preferred embodiment of the invention, the electronics module 6 further comprises a data transmission sub-system that is programmed and configured to control the transmission of signals from the respiratory parameter monitoring sub-system 2 and physiological parameter monitoring sub-system 4*a*.

In some embodiments, the data transmission sub-system is also preferably programmed and configured to transmit the respiratory parameter signals to a remote signal receiving device, e.g., a base module or a hand-held electronic device, such as a smart phone, tablet, computer, etc. In some embodiments, the remote signal receiving device is programmed and configured to display received and/or processed signals, e.g., respiration parameter signals, physiological parameter signals and accelerometer data received from the electronics module 6.

As further illustrated in FIG. 2, the respiratory-physiological parameter monitoring system 102 also similarly includes signal transmission conductors 8, which facilitate connection and, thereby, signal communication by and between the respiratory parameter monitoring sub-system 2, physiological parameter monitoring sub-system 4*a*, and electronics module 6.

Figure 3:
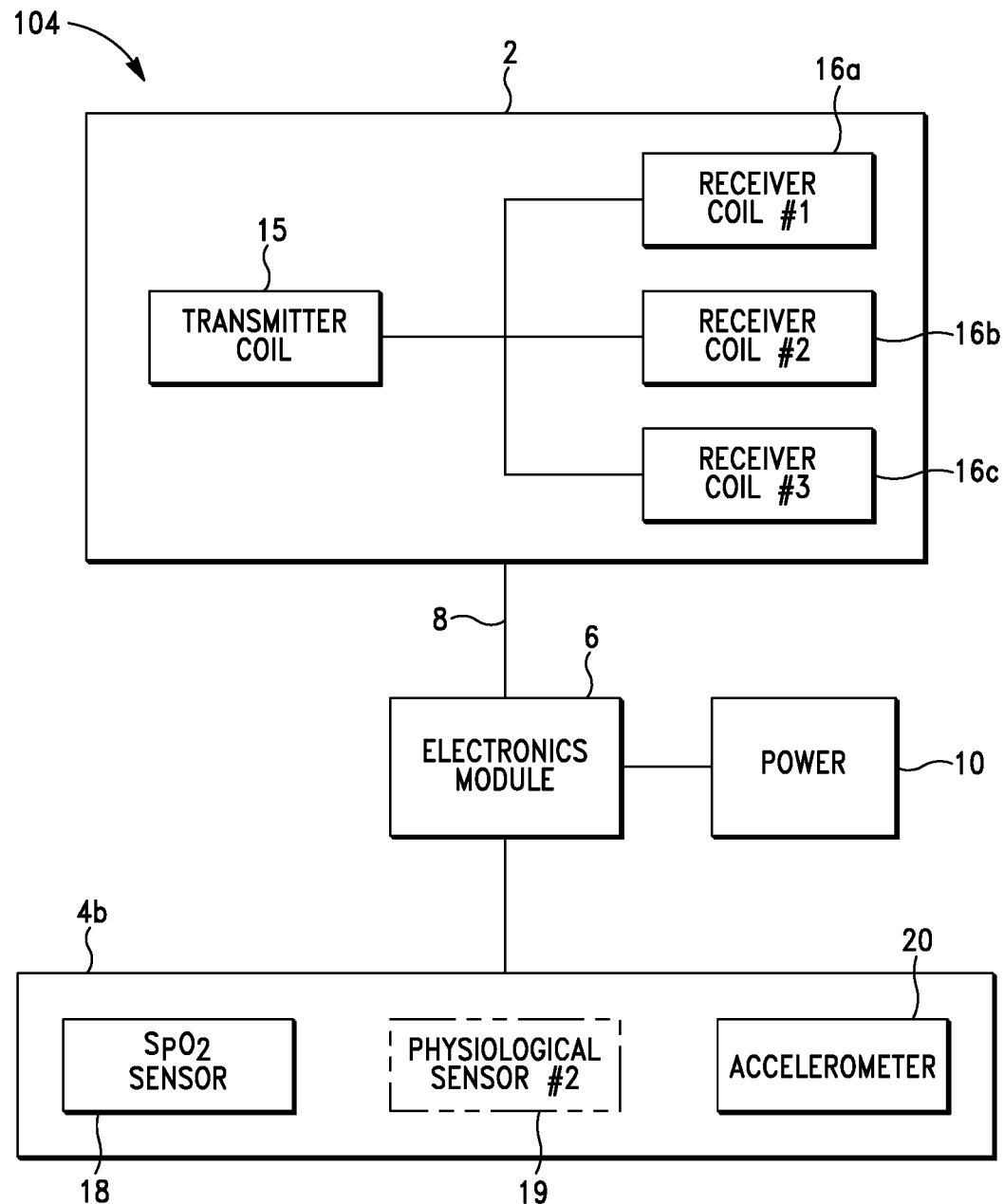
FIG. 3 is a schematic illustration of yet another embodiment of a physiological monitoring system, in accordance with the invention.

Referring now to FIG. 3, there is shown a schematic illustration of another embodiment of a respiratory-physiological parameter monitoring system of the invention. As illustrated in FIG. 3, the respiratory-physiological parameter monitoring system 104 similarly preferably comprises a respiratory parameter monitoring sub-system 2, a physiological parameter monitoring sub-system comprising at least one physiological parameter monitoring sensor, electronics module 6, signal transmission conductors 8, and a power source 10, such as embodied in the respiratory-physiological parameter monitoring system 102 described above.

As further illustrated in FIG. 3, in this embodiment, the physiological parameter monitoring sub-system (now denoted "4b") further comprises an accelerometer 20 that is preferably configured detect and monitor anatomical positions and physical movement of the subject, and generate and transmit accelerometer signals representing same, including accelerometer data representing at least one anatomical position of the subject.

In this embodiment, the processing system of the electronics module 6 is also programmed to determine a respiratory disorder as a function of measured respiratory and physiological parameters, and accelerometer data of the subject, and at least one anatomical position of the subject as a function of the accelerometer data.

Figure 4:
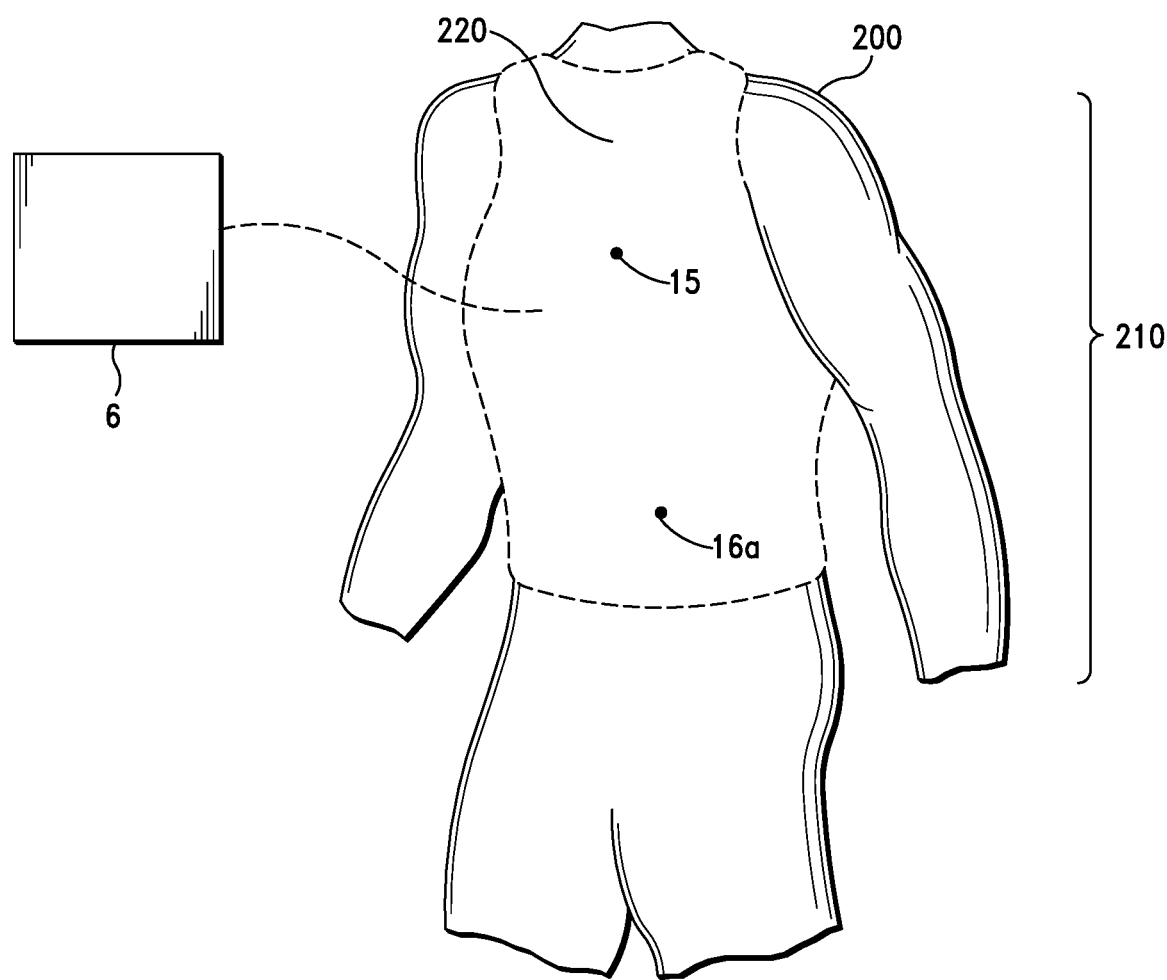
FIG. 4 is a perspective view of one embodiment of a wearable physiological monitoring system positioned on a subject showing the position of a transmitter coil proximate the xyphoid process and one (1) receiver coil proximate the umbilicus, in accordance with the invention.

Referring now to FIG. 4, there is shown an embodiment of a wearable garment 220 that can incorporate a monitoring system of the invention, including monitoring systems 100 and 102 shown in FIGS. 1-3.

As indicated above and illustrated in FIG. 4, the wearable garment 220 is preferably configured to cover at least the upper torso 210, i.e., the thoracic and abdominal regions, of a subject 200.

According to the invention, the wearable garment 220 can, however, also be configured to cover other regions of the subject 200, including, without limitation, the lower abdominal region.

Figure 5:
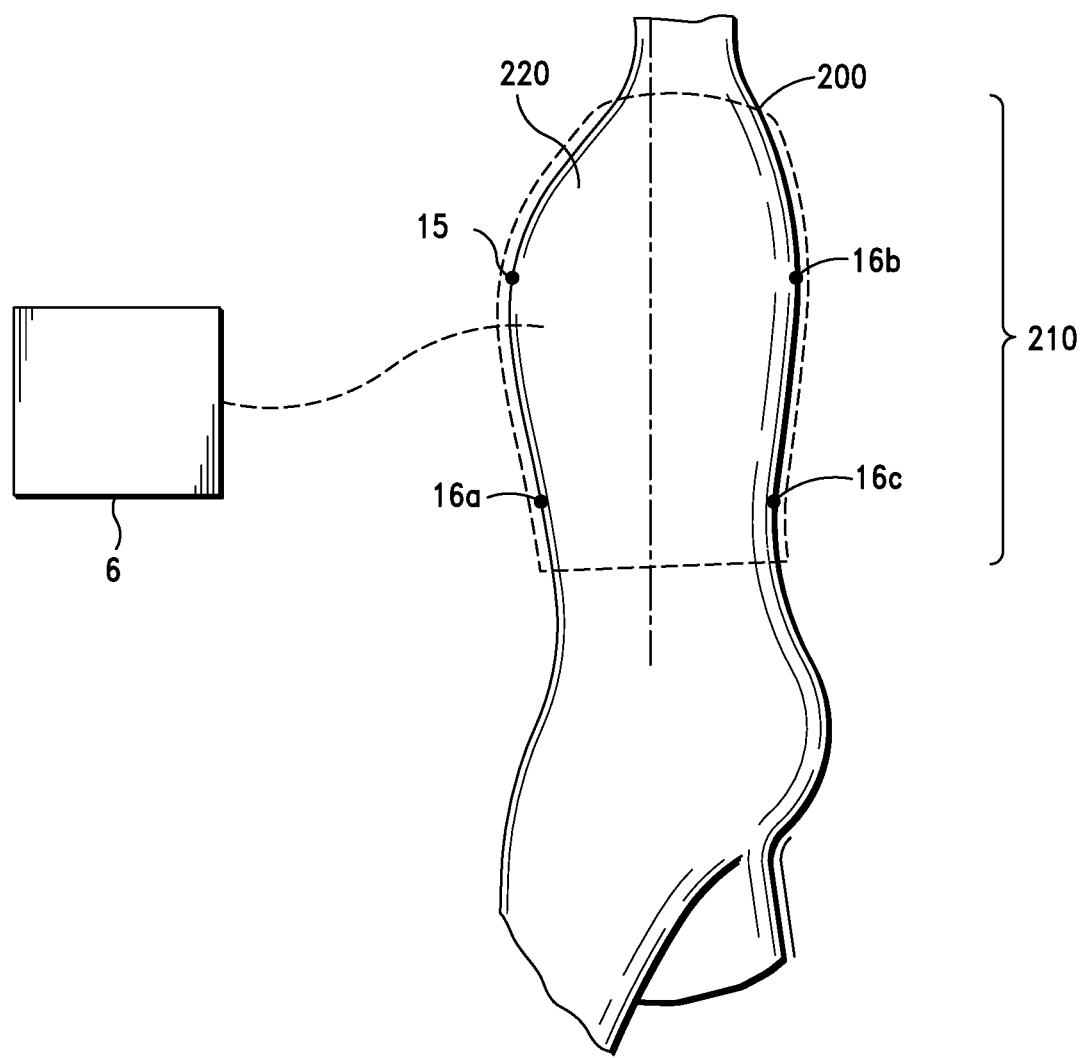
FIG. 5 is a side view of a subject, showing the position of a transmitter coil and three (3) receiver coils in a wearable physiological monitoring system and, thereby, on the subject, in accordance with one embodiment of the invention.

As illustrated in FIG. 5, in a preferred embodiment, when the wearable garment 220 incorporates a monitoring system of the invention (and, hence, forms a wearable monitoring system) and is positioned on the upper torso 210 of a subject, the transmitter coil 15 is preferably positioned proximate the subject's xyphoid process and the first receiver coil 16a is positioned proximate the umbilicus, the second receiver coil 16b is positioned proximate the subject's spine opposite the transmitter coil 15, and the third receiver coil 16c is positioned proximate the subject's spine opposite the umbilicus.

According to the invention, when the noted wearable monitoring system is positioned proximate the upper torso 210 of a subject 200 and the monitoring system is initiated, respiratory disorders and anatomical positions of the subject 200 can be accurately determined.

As will readily be appreciated by one having ordinary skill in the art, the present invention provides numerous advantages compared to prior art methods and systems for determining respiratory characteristics and respiratory disorders therefrom, and anatomical positions and movement of a subject.

Among the advantages are the following:

The provision of wearable physiological monitoring systems that accurately detect and measure respiratory parameters and/or characteristics in real time based on anatomical displacements of a monitored subject.

The provision of wearable physiological monitoring systems that that accurately determine anatomical positions of a subject.

The provision of wearable physiological monitoring systems that train a subject to maintain an anatomical position during sleep that is less likely to exacerbate and/or trigger a symptom of an existing respiratory or sleep disorder of the subject.

The provision of improved methods for determining a respiratory disorder based on detected respiratory and/or physiological parameters and/or characteristics.

The provision of improved methods for determining sleep apnea and/or hypopnea based on detected abnormal respiratory and/or physiological parameters and/or characteristics.

The provision of methods for training a subject to maintain an anatomical position during sleep that is less likely to exacerbate and/or trigger a symptom of an existing respiratory or sleep disorder of the subject.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A wearable physiological parameter monitoring system, comprising:

a wearable garment that is configured to be removably positioned on an upper torso of said subject, whereby said wearable garment covers said upper torso of said subject, said upper torso region of said subject comprising at least first and second anatomical regions, said physiological monitoring system comprising a power source, respiratory parameter monitoring sub-system, a physiological parameter sub-system, and an electronics module, said power source, respiratory parameter monitoring sub-system and physiological parameter sub-system being in communication with said electronics module, said physiological parameter sub-system comprising an accelerometer configured to detect anatomical positions and movement of said subject, and generate and transmit accelerometer signals representing same, said respiratory parameter monitoring sub-system comprising a transmitter coil and a receiver coil, said transmitter coil and receiver coil being positioned on said wearable garment, whereby, when said wearable garment is positioned on said subject, said transmitter coil is positioned proximate said first anatomical region of said subject's upper torso and said receiver coil is positioned proximate said second anatomical region of said subject's upper torso in axial alignment with said transmitter coil, said transmitter coil being adapted to generate a plurality of alternating current (AC) magnetic fields in a plurality of field dimensions, said plurality of field dimensions comprising a plurality of field dimension frequencies, said plurality of AC magnetic fields comprising a first AC magnetic field comprising first, second and third field dimensions, said first, second and third field dimensions of said first AC magnetic field comprising a first field frequency of said plurality of field dimension frequencies, said first field dimension of said first AC magnetic field comprising a first variable strength as a function of a first distance of said receiver coil from said transmitter coil, said second field dimension of said first AC magnetic field comprising a second variable strength as a function of a second distance of said receiver coil from said transmitter coil, and said third field dimension of said first AC magnetic field dimension comprising a third variable strength as a function of a third distance of said receiver coil from said transmitter coil, said receiver coil being configured to detect and measure said first, second and third variable field strengths in said first, second and third field dimensions of said first AC magnetic field, said receiver coil being further configured to generate a first AC magnetic field strength signal representing said first variable field strength in said first field dimension of said first AC magnetic field, a second AC magnetic field strength signal representing said second variable field strength in said second field dimension of said first AC magnetic field, and a third AC magnetic field strength signal representing said third variable field strength in said third field dimension of said first AC magnetic field, and transmit said first, second and third AC magnetic field strength signals to said electronics module, said electronics module being adapted to receive said first, second and third AC magnetic field strength signals transmitted by said receiver coil and said accelerometer signals transmitted by said accelerometer, said electronics module comprising a processing system that is programmed and configured to determine at least one respiratory parameter of said subject as a function of said first, second and third AC magnetic field strength signals transmitted by said receiver coil and said accelerometer signals transmitted by said accelerometer, said processing system being further programmed and configured to determine a value of said at least one respiratory parameter of said subject as a function of said first, second and third AC magnetic field strength signals transmitted by said receiver coil and said accelerometer signals transmitted by said accelerometer, said processing system being further programmed and configured to determine at least one respiratory disorder of said subject as a function of said determined at least one respiratory parameter and said determined value thereof.

2. The system of claim 1, wherein said electronics module is further programmed and configured to determine at least one anatomical position of said subject as a function of said first, second and third AC magnetic field strength signals and said accelerometer signals.

3. The system of claim 1, wherein said physiological parameter sub-system further comprises a $SpO^2$ sensor configured to detect and measure blood oxygen saturation levels of said subject, and generate and transmit $SpO^2$ signals representing same to said electronics module.

4. The system of claim 3, wherein said electronics module is further programmed and configured to determine said at least one respiratory parameter and value thereof of said subject as a function of said first, second and third AC magnetic field strength signals transmitted by said receiver coil, said accelerometer signals transmitted by said accelerometer and said $SpO_2$ signals, and said at least one respiratory disorder of said subject as a function of said determined at least one respiratory parameter and said determined value thereof.

5. The system of claim 1, wherein said first anatomical region of said subject comprises a thoracic region of said subject and said second anatomical region comprises an abdominal region of said subject.

6. The system of claim 1, wherein said electronics module is further programmed and configured to generate at least one respiratory disorder warning signal that induces an excitation event when said determined at least one respiratory parameter exceeds a predetermined respiratory parameter threshold.

7. The system of claim 6, wherein said at least one respiratory parameter comprises an apnea/hypopnea index (AHI) of said subject, and wherein said predetermined respiratory parameter threshold comprises an AHI score in the range of 5-15 apneic events per hour of said subject's sleep.

8. The system of claim 6, wherein said at least one respiratory parameter comprises minute ventilation of said subject, and wherein said predetermined respiratory parameter threshold comprises a reduction of said subject's minute ventilation of at least 30% of said subject's average normal minute ventilation.

9. The monitoring system of claim 6, wherein said at least one respiratory parameter comprises a breathing rate of said subject, and wherein said predetermined respiratory parameter threshold comprises cessation in said subject's breathing for at least 10 seconds.

10. The system of claim 1, wherein said at least one respiratory parameter of said subject comprises an apnea.

11. A method for determining a respiratory disorder of a subject, comprising the steps of:
(i) providing a wearable physiological monitoring system that is configured to be removably positioned on an upper torso of said subject, whereby said physiological monitoring system covers said upper torso of said subject, said upper torso region of said subject comprising at least first and second anatomical regions, said physiological monitoring system comprising a power source, respiratory parameter monitoring sub-system, a physiological parameter sub-system, and an electronics module, said power source, respiratory parameter monitoring sub-system and physiological parameter sub-system being in communication with said electronics module, said physiological parameter sub-system comprising an accelerometer configured to detect anatomical positions and movement of said subject, and generate and transmit accelerometer signals representing same, said respiratory parameter monitoring sub-system comprising a transmitter coil and a receiver coil, said transmitter coil and receiver coil being positioned on said wearable garment, whereby, when said wearable garment is positioned on said subject, said transmitter coil is positioned proximate said first anatomical region of said subject's upper torso and said receiver coil is positioned proximate said second anatomical region of said subject's upper torso in axial alignment with said transmitter coil, said transmitter coil being adapted to generate a plurality of alternating current (AC) magnetic fields in a plurality of field dimensions, said plurality of field dimensions comprising a plurality of field dimension frequencies, said plurality of AC magnetic fields comprising a first AC magnetic field comprising first, second and third field dimensions, said first, second and third field dimensions of said first AC magnetic field comprising a first field frequency of said plurality of field dimension frequencies, said first field dimension of said first AC magnetic field comprising a first variable strength as a function of a first distance of said receiver coil from said transmitter coil, said second field dimension of said first AC magnetic field comprising a second variable strength as a function of a second distance of said receiver coil from said transmitter coil, and said third field dimension of said first AC magnetic field dimension comprising a third variable strength as a function of a third distance of said receiver coil from said transmitter coil, said receiver coil being configured to detect and measure said first, second and third variable field strengths in said first, second and third field dimensions of said first AC magnetic field, said receiver coil being further configured to generate a first AC magnetic field strength signal representing said first variable field strength in said first field dimension of said first AC magnetic field, a second AC magnetic field strength signal representing said second variable field strength in said second field dimension of said first AC magnetic field, and a third AC magnetic field strength signal representing said third variable field strength in said third field dimension of said first AC magnetic field, and transmit said first, second and third AC magnetic field strength signals to said electronics module, said electronics module being adapted to receive said first, second and third AC magnetic field strength signals transmitted by said receiver coil and said accelerometer signals transmitted by said accelerometer, said electronics module comprising a processing system that is programmed and configured to determine at least one respiratory parameter of said subject as a function of said first, second and third AC magnetic field strength signals transmitted by said receiver coil and said accelerometer signals transmitted by said accelerometer, said processing system being further programmed and configured to determine a value of said at least one respiratory parameter of said subject as a function of said first, second and third AC magnetic field strength signals transmitted by said receiver coil and said accelerometer signals transmitted by said accelerometer, said processing system being further programmed and configured to determine at least one respiratory disorder of said subject as a function of said determined at least one respiratory parameter and said determined value thereof, (ii) positioning said monitoring system on a first subject;
(iii) initiating said monitoring system via said power source, wherein said first AC magnetic field is generated and transmitted by said transmitter coil;
(iv) detecting and measuring said first, second and third variable field strengths in said first, second and third field dimensions of said first AC magnetic field with said receiver coil;
(v) generating said first, second and third AC magnetic field strength signals with said receiver coil;
(vi) measuring accelerometer data with said accelerometer and generating said accelerometer signals representing said accelerometer data;
(vii) transmitting said first, second and third AC magnetic field strength signals to said electronics module with said first receiver coil;
(viii) transmitting said accelerometer signals to said electronics module with said accelerometer;
(ix) determining at least one respiratory parameter and value thereof of said first subject as a function of said first, second and third AC magnetic field strength signals and said accelerometer signals with said electronics module; and
(x) determining at least one respiratory disorder of said first subject as a function of said determined at least one respiratory parameter and said determined value thereof with said electronics module.

12. The method of claim 11, wherein said electronics module is further programmed and configured to determine at least one anatomical position of said subject as a function of said first, second and third AC magnetic field strength signals and said accelerometer signals.

13. The method of claim 12, wherein the method further comprises the step of determining at least a first anatomical position of said subject as a function of said first, second and third AC magnetic field strength signals and said accelerometer signals.

14. The method of claim 11, wherein said physiological parameter sub-system further comprises a $SpO^2$ sensor configured to detect and measure blood oxygen saturation levels of said subject, and generate and transmit $SpO^2$ signals representing same.

15. The method of claim 14, wherein said electronics module is further programmed and configured to determine said at least one respiratory parameter and value thereof of said subject as a function of said first, second and third AC magnetic field strength signals transmitted by said receiver coil, said accelerometer signals transmitted by said accelerometer and said $SpO^2$ signals, and said at least one respiratory disorder of said subject as a function of said determined at least one respiratory parameter and said determined value thereof.

16. The method of claim 15, wherein the method further comprises the steps of detecting and measuring at least a first blood oxygen saturation level of said subject with said $SpO^2$ sensor, generating and transmitting at least a first $SpO^2$ signal representing said at least a first blood oxygen saturation level of said subject to said electronics module with said $SpO^2$ sensor, determining said at least one respiratory parameter and value thereof of said subject as a function of said first, second and third AC magnetic field strength signals transmitted by said receiver coil, said accelerometer signals transmitted by said accelerometer and said $SpO^2$ signals, and determining said at least one respiratory disorder of said subject as a function of said determined at least one respiratory parameter and said determined value thereof.

17. The method of claim 11, wherein said first anatomical region of said subject comprises a thoracic region of said subject and said second anatomical region comprises an abdominal region of said subject.

18. The method of claim 11, wherein said at least one respiratory parameter of said subject comprises an apnea.

* * * * *